United States Patent [19]

Amano et al.

[11] Patent Number: 5,608,119

[45] Date of Patent: Mar. 4, 1997

[54] (2S)-3-[(1R, 2S, 5R)-[5-METHYL-2-(1-METHYLETHYL)-CYCLOHEXYL]OXY]-1, 2-PROPANEDIOL, PROCESS FOR PRODUCING THE SAME, AND COMPOSITIONS CONTAINING THE SAME

[75] Inventors: Akira Amano; Kazuhiko Tokoro, both of Kanagawa, Japan

[73] Assignee: Takasago International Corporation, Tokyo, Japan

[21] Appl. No.: 463,896

[22] Filed: Jun. 5, 1995

Related U.S. Application Data

[62] Division of Ser. No. 305,883, Sep. 14, 1994, abandoned.

[30] Foreign Application Priority Data

Sep. 16, 1993 [JP] Japan ..................... 5-252184

[51] Int. Cl.$^6$ .................................................. C07C 41/00
[52] U.S. Cl. ........................................................ 568/676
[58] Field of Search .................................................. 568/670

[56] References Cited

FOREIGN PATENT DOCUMENTS

| | | | |
|---|---|---|---|
| 60-25908 | 2/1985 | Japan | A61K 7/00 |
| 62-96403 | 5/1987 | Japan | A61K 7/00 |
| 62-192312 | 8/1987 | Japan | A61K 7/06 |
| 63-208505 | 8/1988 | Japan | A61K 7/00 |
| 63-264522 | 11/1988 | Japan | A61K 31/08 |

*Primary Examiner*—Ngoclan Mai
*Assistant Examiner*—Anthony R. Chi
*Attorney, Agent, or Firm*—Sughrue, Mion, Zinn, Macpeak & Seas

[57] ABSTRACT

(2S)-3-{(1R, 2S, 5R)-[5-Methyl-2-(1-methylethyl)cyclohexyl]oxy}-1,2-propanediol represented by the following formula (I);

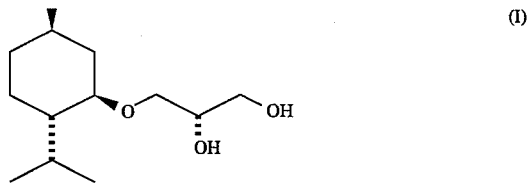

(I)

a process of producing the (2S)-3-{(1R, 2S, 5R)-[5-methyl-2-(1-methylethyl)cyclohexyl]oxy}-1,2-propanediol which comprises adding (1R, 2S, 5R)-5-methyl-2-(1-methylethyl) cyclohexyl alcohol to (R)-(−)-benzyl glycidyl ether to provide (2S)-1-benzyloxy-2-hydroxy-3-{(1R, 2S, 5R)-[5-methyl-2-(1-methylethyl)cyclohexyl]oxy}propane, and hydrogenolyzing the product, are disclosed.

1 Claim, No Drawings

(2S)-3-[(1R, 2S, 5R)-[5-METHYL-2-(1-METHYLETHYL)-CYCLOHEXYL]OXY]-1, 2-PROPANEDIOL, PROCESS FOR PRODUCING THE SAME, AND COMPOSITIONS CONTAINING THE SAME

This is a Divisional of application Ser. No. 08/305,883 filed Sep. 14, 1994 now abandoned.

FIELD OF THE INVENTION

The present invention relates to (2S)-3-{(1R, 2S, 5R)-[5-methyl-2-(1-methylethyl)cyclohexyl]oxy}-1,2-propanediol having an activity of giving an excellent cool or refreshing feeling to the skin and the mucous membrane of a human being, a production process thereof, and compositions for oral cavity, food and drink compositions, cosmetic compositions, etc., comprising the compound.

BACKGROUND OF THE INVENTION

In general, useful physiologically active substances having an asymmetric structure are frequently specific antipodes and the tendency is remarkable in the fields of medicaments, agricultural chemicals, food additives, etc. For example, (1R, 2S, 5R)-5-methyl-2-(1-methylethyl)cyclohexyl alcohol (hereinafter, is referred to as "l-menthol") has a strong peppermint smell with a cool feeling activity and is used as a flavor but it is known that d-menthol which is an optical antipode is poor in a refreshing feeling and has a sweet flavor a little [Motoichi Indo, *Koryo no Jissai Chishiki (Actual Knowledge of Perfume)*, page 79, published by Toyo Keizai Sinpo Sha, 1975].

On the other hand, U.S. Pat. No. 4,459,425 discloses 3-{(1R, 2S, 5R)-[5-methyl-2-(1-methylethyl)oxy-1,2-propanediol (the compound is also called "3-l-menthoxypropane-1,2-diol").

According to the description of the U.S. patent described above, 3-l-menthoxypropane-1,2-diol is obtained by forming the sodium salt of l-menthol with metallic sodium or sodium hydride, reacting the sodium salt with allyl halide to provide 3-l-menthoxypropan-1-ene, oxidizing the product using an organic peracid to form an oxide, and then hydrolyzing the oxide.

Also, according to the description of the foregoing U.S. patent, since 3-l-menthoxypropane-1,2-diol has a property of giving a cool-feeling activity but does not have a smell different from l-menthol, for the purpose of imparting a cool-feeling activity to an article without giving any influence to the flavor of the article by utilizing the foregoing property, the compound is compounded with compositions for oral cavity such as a tooth powder, a wet tooth powder, a tooth paste, a chewing gum, etc., or food and drink such as a sherbet, a hard candy, etc.

Furthermore, it is proposed to compound the foregoing compound with cosmetics such as cosmetic materials as described in JP-A-60-25908 and JP-A-63-208505 (the term "JP-A" as used herein means an "unexamined published Japanese patent application"), eye pack agents as described in JP-A-62-96403, hair cosmetic materials as described in JP-A-62-192312, etc., and also with aerosol compositions for anti-inflammatory analgesic agents as described in JP-A-63-264522, etc.

However, the 3-l-menthoxypropane-1,2-diols disclosed in the specifications of the foregoing patent applications are compounds wherein the asymmetric center at the 2-position of the propanediol in molecule is uncertain. In the production process described in U.S. Pat. No. 4,459,425 described above, three asymmetric centers in the l-menthol structure of the four asymmetric centers in the molecule of 3-l-menthoxypropane-1,2-diol are confirmed but no steric control of the 2-position of the propanediol is made and a racemic modification only, which is an equivalent mixture of the (2S) isomer and the (2R) isomer, can be synthesized.

There are no examples that the (2R) isomer of 3-l-menthoxypropane-1,2-diol is isolated from the (2S) isomer thereof and that they are synthesized and properties of them are compared and confirmed, and also there are no reports about various compositions containing them.

SUMMARY OF THE INVENTION

Thus, the object of the present invention is to establish a useful production process of the antipode having a more excellent cool-feeling activity than the cool-feeling activity of a conventional racemic modification by synthesizing both the antipodes, i.e., the (2S) isomer and the (2R) isomer of 3-l-menthoxypropane-1,2-diol and selecting the useful antipode, and further to provide various compositions utilizing the property of the foregoing antipode.

As the result of various investigations under the circumstances described above, the present inventors have discovered that by using (R)- or (S)-benzyl glycidyl ether and l-menthol, that is, (1R, 2S, 5R)-5-methyl-2-(1-methylethyl) cyclohexyl alcohol as raw materials, the (2S) isomer and the (2R) isomer of 3-l-menthoxypropane-1,2-diol, that is, (2S)-3-{(1R, 2S, 5R)-[5-methyl-2-(1-methylethyl)cyclohexyl]oxy}-1,2-propanediol and (2R)-3-{(1R, 2S, 5R)-[5-methyl-2-(1-methylethyl)cyclohexyl]oxy}-1,2-propanediol can be separately and easily synthesized and that when the cool-feeling activity of both the antipodes obtained were compared with each other by expert panelists, the (2S) isomer has a more excellent cool-feeling activity than the cool-feeling activity of the (2R) isomer and also than the cool-feeling activity of the conventional racemic modification.

Furthermore, it has also been discovered that by compounding the (2S) isomer with compositions for oral cavity, food and drink, and cosmetics, various compositions capable of giving a sufficient cool-feeling and refreshing feeling can be obtained with a less compounding amount thereof than the case of compounding a conventional racemic modification, and the inventors have, thus, accomplished the present invention based on the discoveries.

That is, according to an aspect of the present invention, there is provided (2S)-3-{(1R, 2S, 5R)-[5-methyl2-(1-methylethyl)cyclohexyl]oxy}-1,2-propanediol represented by formula (I).

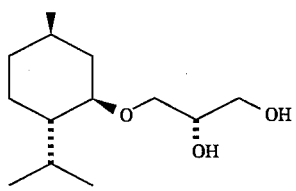

According to other aspect of the present invention, there is provided a production process of the compound described above.

According to another aspect of the present invention, there are provided compositions for oral cavity, food and drink, and cosmetics each compounded with the compound described above.

DETAILED DESCRIPTION OF THE INVENTION

Then, the present invention is described in detail.

The production process of (2S)-3-{(1R, 2S, 5R)-[5-methyl-2-(1-methylethyl)cyclohexyl]oxy}-1,2-propanediol (hereinafter, is referred to as "(2S)-3-l-menthoxypropane-1,2-diol") of the present invention shown by formula (I) described above is shown by the following reaction formula.

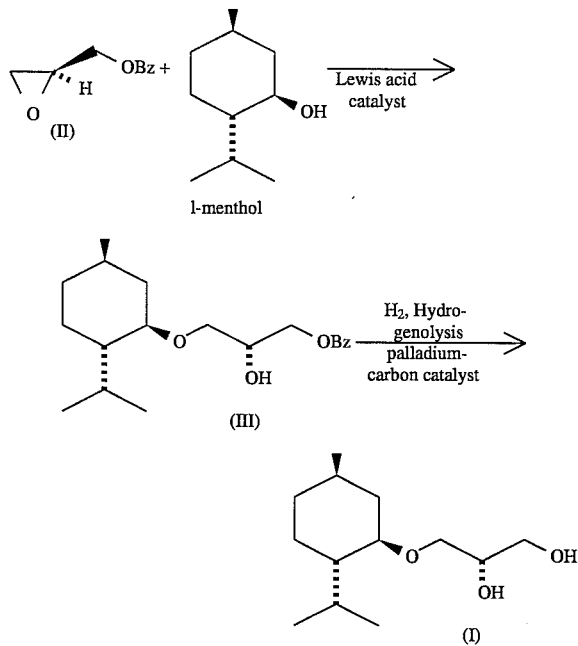

wherein Bz represents a benzyl group.

That is, (2S)-3-l-menthoxypropane-1,2-diol can be obtained by adding (1R, 2S, 5R)-5-methyl-2-(1-methylethyl)cyclohexyl alcohol (hereinafter, is referred to as "l-menthol") to (R)–(–)–benzyl glycidyl ether [the compound of formula (II)]in the presence of a Lewis acid catalyst to provide (2S)-1-benzyloxy-2-hydroxy-3-{(1R, 2S, 5R)-[5-methyl-2-(1-methylethyl)cyclohexyl]oxy}propane [the compound of formula (III)], and hydrogenolyzing the compound in the presence of a palladium-carbon catalyst to eliminate the benzyl group.

As (R)–(–)–benzyl glycidyl ether and l-menthol being used as the raw materials, commercially available materials can be used.

There is no particular restriction on the addition reaction method but, for example, the addition reaction may be carried out by adding a proper Lewis acid catalyst to a solution of l-menthol dissolved in a proper solvent and adding dropwise thereto a solution of (R)–(–)–benzyl glycidyl ether dissolved in a proper solvent to cause the reaction.

The using amount of t-menthol is preferably from about 1 to 2 mol times, and more preferably from about 1.3 to 1.5 mol times to 1 mol of (R)–(–)–benzyl glycidyl ether.

The using amount of the Lewis acid catalyst may be a catalytic amount in an ordinary addition reaction and is preferably from about 0.01 to 0.1 mol times to 1 mol of (R)–(–)–benzyl glycidyl ether.

As the Lewis acid catalyst being used in this invention, there are a boron fluoride ether complex, aluminum chloride, zinc chloride, zinc bromide, ferric chloride, etc., but the boron fluoride ether complex is particularly preferably used.

As the reaction solvent, there are toluene, xylene, petroleum ether, tetrahydrofuran, etc., but toluene is particularly preferably used.

The reaction temperature of the addition reaction is preferably from about 30° to 50° C., and particularly preferably about 45° C. It is preferred to carry out the reaction for from about 2 to 3 hours at the temperature.

(2S)-1-Benzyloxy-2-hydroxy-3-{(1R, 2S, 5R)-[5-methyl2-(1-methylethyl)cyclohexyl]oxy}propane thus obtained can be subjected to the elimination reaction of the benzyl group without being purified.

The amount of the palladium-carbon catalyst being used for the elimination reaction of the benzyl group is, in the case of using the 5% palladium-carbon catalyst, preferably from about 0.05 to 0.5 g, and more preferably from about 0.05 to 0.1 g to 1 g of (2S)-1-benzyloxy-2-hydroxy-3-{(1R, 2S, 5R)-[5-methyl-2-(1-methylethyl)cyclohexyl] oxy}propane obtained.

Also, as the solvent being used for the elimination reaction, there are methanol, ethanol, isopropanol, etc.

Since the elimination reaction of the benzyl group in the present invention does not proceed under the reaction condition of room temperature and normal pressure being used for an ordinary elimination reaction of the protective group, it is necessary to carry out the elimination reaction at a temperature of at least 70° C. under compressed hydrogen pressure. Practically, the reaction proceeds under the condition of a temperature of from about 70° to 100° C. and a hydrogen pressure of from about 5 to 100 kg/cm$^2$ but it is preferred to carry out the reaction for from about 2 to 3 hours under the condition of about 70° C. and about 50 kg/cm$^2$.

Since the crude product of (2S)-3-l-menthoxypropane-1, 2-diol obtained contains a small amount of a by-product wherein l-menthol is not added to the 3-position but is added to the 2-position of the glycidyl group, that is, 2-l-menthoxypropane-1,3-diol by-produced in the addition reaction described above, the product is purified by removing such an impurity by, for example, silica gel column chromatography.

As described above, the compound of the present invention, (2S)-3-l-menthoxypropane-1,2-diol can be synthesized by an easy operation using easily available raw materials.

The cool-feeling activity of the compound of the present invention, (2S)-3-l-menthoxypropan-1,2-diol obtained as described above is superior to that of (2R)-3-l-menthoxypropane-1,2-diol, which is an antipode and that of the conventional racemic modification, as will be described later. In addition, (2R)-3-l-menthoxypropane-1,2-diol can be obtained by synthesizing as the case of producing the compound of the present invention except that commercially available (S)–(+)–benzyl glycidyl ether is used in place of (R)–(–)–benzyl glycidyl ether as the raw material.

The compound of the present invention, (2S)-3-l-menthoxypropane-1,2-diol the excellent cool-feeling activity of which has been confirmed as described above can be used in a wide range as conventional cool-feeling agents without particular restrictions. That is, by compounding the compound of this invention with a composition for oral cavity, a food and drink composition, a cosmetic composition, etc., by expecting the cool-feeling or the refreshing feeling, the commercial value thereof can be increased.

As the compositions for oral cavity of the present invention, there are various forms such as a gargle, a chewing gum, etc., in addition to dentifrices such as a tooth powder, a wet tooth powder, a tooth paste, etc. The compounding amount of the compound of the present invention, (2S)-3-l-menthoxypropane-1,2-diol in such a composition for oral cavity depends upon the form but is preferably from about 0.01 to 0.5% by weight of the amount of the whole composition.

Also, as other components, optional components according to the using purpose can be used.

For example, in the case of chewing gum, in addition to a gum base, sweeteners such as sugar, stevioside, etc.; flavor materials such as peppermint, spearmint, l-menthol, carvone, anethole, etc.; and effective components such as flavonoid, etc., can be properly compounded according to an ordinary manner. Similarly, in the cases of dentifrices, gargles, etc., components according to the kind of the product can be properly compounded therewith.

As the food and drink of the present invention, there are forms such as an ice cream, a sherbet, a jelly, a hard candy, a soft drink, etc., and the compounding amount of the compound of the present invention, (2S)-3-l-menthoxypropane-1,2-diol in such a food and drink depends upon the form thereof but is preferably from about 0.01 to 0.5% by weight of the amount of the whole composition.

For example, in the case of a hard candy, in addition to the bases such as fine granulated sugar, a starch syrup, water, etc.; flavor materials such as soda flavor, etc., can be properly compounded according to an ordinary manner. Similarly, in the cases of an ice cream, a sherbet, a jelly, a soft drink, etc., components according to the kind of the product can be properly compounded therewith.

As the cosmetics of the present invention, there are various lotions such as an astringent lotion, an after shaving lotion, a milky lotion, etc.; various creams such as a massage cream, a nutritious cream, etc.; various packs such as an eye pack agent, a pasty cleansing pack agent, etc.; hair cosmetics such as a hair tonic, a pomade, a shampoo, a rinse, a hair treatment, a hair cream, etc.; face cleansing soaps and other soaps; anhidrotics; deodorants; etc. The compounding amount of the compound of the present invention, (2S)-3-l-menthoxypropane-1,2-diol depends upon the form thereof but is preferably from about 0.5% to 10% by weight of the whole component.

Also, as other component(s), optional component(s) according to the using purpose can be used.

For example, in the case of creams, in addition to an emulsifying agent, a perfume, an antiseptic, a pigment, etc., if necessary, a nutrient, a wetting agent, an ultraviolet inhibitor, etc., can be properly compounded therewith according to an ordinary manner.

Similarly, in the cases of lotions, milky lotions, packs, hair cosmetics, soaps, anhidrotics, deodorants, etc., components according to the kind of the product can be properly compounded therewith.

Furthermore, the compound of the present invention is expected to be compounded with medical supplies. For example, it is expected to use the compound of the present invention for medicines for external use, such as, for example, aerosol preparations, cataplasms, ointments, etc.

Then, the following examples are intended to illustrate the present invention practically but not to limit the invention in any way.

In addition, the analyses in the examples were carried out using the following analytical instruments.

Gas chromatogram: 5890-A (trade name, manufactured by Hewlett-Packard Co.)

Column: Chemical bonded column OV-1, 25 mm×0.25 mm, ID 0.15 mm (manufactured by GL Science K. K.)

Temperature: 70° to 220° C. (raised at 4° C./minute)

Angle of Rotation: DIP-370 (manufactured by JASCO Inc.)

Proton Nuclear Magnetic Resonance Spectra ($^1$H-NMR): AM-400 (400 MHz) (manufactured by Bruker, Inc.)

EXAMPLE 1

Production of (2S)-3-t-menthoxypropane-1,2-diol:

In a reaction vessel the inside atmosphere of which was previously replaced with a nitrogen gas were placed 14 g (90 mmols) of l-menthol (made by Takasago International Corporation), 29 ml of toluene, and 0.12 g (0.85 mmol) of a boron trifluoride ether complex and the mixture was heated to 5° C. To the solution was added dropwise a solution of 10 g (61 mmols) of (R)-(-)-benzyl glycidyl ether (made by Daiso Co., Ltd.) dissolved in 12 ml of toluene over a period of 40 minutes while maintaining at the same temperature. Thereafter, the reaction was further carried out for 2 hours while maintaining at the same temperature.

After the reaction was over, the reaction mixture was washed with a saturated aqueous sodium chloride solution and after dehydrating with anhydrous magnesium sulfate, a toluene layer formed was recovered and concentrated. The concentrate was further distilled under high vacuum to distill off the excess of l-menthol having a boiling point lower than that of the reaction product, whereby 16.1 g of the crude product of (2S)-1-benzyloxy-2-hydroxy-3-[(1R,2S, 5R)-[5-methyl-2-(1-methylethyl)cyclohexyl]oxy]propane was obtained.

In an autoclave were placed 16.1 g of the crude product of (2S)-1-benzyloxy-2-hydroxy-3-[(1R, 2S, 5R)-[5-methyl-2-(1-methylethyl)cyclohexyl]oxy]propane obtained, 2 g of a 5% palladium-carbon catalyst, and 60 ml of ethanol and the initial hydrogen pressure and the established temperature were adjusted to 50 kg/cm$^2$ and 70° C., respectively to initiate the hydrogenolysis reaction. After about 3 hours since the reaction temperature reached 70° C., it was confirmed that the stoichiometric amount of hydrogen was absorbed and then the reaction was stopped.

After cooling the reaction vessel to room temperature, the hydrogen gas in the vessel was discharged, after further replacing the inside atmosphere in the vessel with a nitrogen gas, the vessel was opened, and the reaction mixture was recovered. After filtering the reaction mixture to separate the catalyst and ethanol was recovered by distillation to provide 12 g of a crude product.

The composition of the crude product by gas chromatogram was 80% (2S)-3-l-menthoxypropane-1,2-diol (the yield to (R)-(-)-benzyl glycidyl ether was 69%), 9.5% 2-l-menthoxypropane-1,3-diol as a by-product, and 8.7% l-menthol as the raw material.

The crude product was purified using a column packed with silica gel by an n-hexane wet method. As the development solvent, a mixed solvent composed of ethyl acetate and n-hexane was used and it was tried to increase the purity of (2S)-3-l-menthoxypropane-1,2-diol eluted by gradually increasing, in succession, the mixing ratio of ethyl acetate from 5% by volume to 15% by volume.

Thereby, (2S)-3-l-menthoxypropane-1,2-diol was eluted at the highest purity in the fraction obtained from the development solvent containing from 10 to 11% by volume ethyl acetate and the amount of (2S)-3-l-menthoxypropane-1,2-diol in the fraction was 4.4 g (the yield to (R)-(-)-benzyl glycidyl ether was 31%).

The properties of the product were as follows.

Purity: 99.4% (Measured by gas chromatogram.)

Optical purity: 99% (The purity was determined by the integrated value of the signal of one proton in the two protons existing at the 3-position of the propane group of (2S)-3-l-menthoxypropane-1,2-diol in the NMR spectra. In addition, the chemical shift of the signal was 3.37 ppm.)

Specific rotation: $[\alpha]^{25}_D = -88.0°$ (c=1, ethanol)

$^1$H-NMR(CDCl$_3$) δ ppm: 0.78 (doublet, 3H, the protons of the methyl group at the 7-position of the menthane skeleton) 0.81–1.3 (multiplet, 2H the axial protons of the methylenes at the 5-position and the 6-position of the menthane skeleton) 0.90 (doublet, 3H, the protons of the methyl group at the 9-position or the 10-position of the menthane skeleton) 0.92 (doublet, 3H, the protons of the methyl group at the 9-position or the 10-position of the menthane skeleton) 1.21–1.28 (multiplet, 1H, the axial proton of the methylene at the 2-position of the menthane skeleton) 1.29–1.42 (multiplet, 1H, the proton of the methine at the 4-position of the menthane skeleton) 1.59–1.62 (multiplet, 2H, the equatorial protons of the methylenes at the 5-position and the 6-position of the menthane skeleton) 2.07–2.18 (multiplet, 2H, the equatorial proton of the methylene at the 2-position and the proton of the methine at the 8-position of the menthane skeleton) 2.37 (doubled doublet, 1H, the proton of the hydroxy group at the 1-position of the propane skeleton) 2.71 (doublet, 1H, the proton of the hydroxy group at the 2-position of the propane skeleton) 3.08 (doubled triplet, 1H, the proton of the methine at the 3-position of the menthane skeleton) 3.37 (doubled doublet, 1H, one of protons of the methylene at the 3-position of the propane skeleton) 3.62–3.75 (multiplet, 3H, one of the protons of the methylene at the 3-position and the protons of the methylene at the 1-position of the propane skeleton) 3.8–3.86 (multiplet, 1H, the proton of the methine at the 2-position of the propane skeleton)

Reference Example 1

Production of (2R)-3-l-menthoxypropane-1,2-diol:

By following the same procedure as Example 1 except that (S)-(+)-benzyl glycidyl ether (made by Daiso Co., Ltd.) in place of (R)-(−)-benzyl glycidyl ether as the raw material compound, (2R)-3-l-menthoxypropane-1,2-diol was obtained.

The properties of the product were as follows.

Purity: 98.5% (Measured by gas chromatogram.)

Optical purity: 99% (The purity was determined by the integrated value of the signal of one proton in two protons existing in the 3-position of the propane group of (2R)-3-l-menthoxypropane-1,2-diol. In addition, the chemical shift of the signal was 3.43 ppm.)

Specific rotation: $[\alpha]^{25}_D = -78.4°$ (c=1, ethanol)

$^1$H-NMR(CDCl$_3$) δ ppm: 0.78 (doublet, 3H, the protons of the methyl group at the 7-position of the menthane skeleton) 0.81–1.3 (multiplet, 2H, the axial protons of the methylenes at the 5-position and the 6-position of the menthane skeleton) 0.90 (doublet, 3H, the protons of the methyl group at the 9-position or the 10-position of the menthane skeleton) 0.92 (doublet, 3H, the protons of the methyl group at the 9-position or the 10-position of the menthane skeleton) 1.21–1.28 (multiplet, 1H, the axial proton of the methylene at the 2-position of the menthane skeleton) 1.29–1.42 (multiplet, 1H, the proton of the methine at the 4-position of the menthane skeleton) 1.59–1.69 (multiplet, 2H, the equatorial protons of the methylenes at the 5-position and the 6-position of the menthane skeleton) 2.07–2.18 (multiplet, 2H, the equatorial proton of the methylene at the 2-position and the proton of the methine at the 8-position of the menthane skeleton) 2.21 (doubled doublet, 1H, the proton of the hydroxy group at the 1-position of the propane skeleton) 2.60 (doublet, 1H, the proton of the hydroxy group at the 2-position of the of the propane skeleton) 3.08 (doubled triplet, 1H, the proton of the methine at the 3-position of the menthane skeleton) 3.43 (doubled doublet, 1H, one of the protons of the methylene at the 3-position of the propane skeleton) 3.63–3.75 (multiplet, 3H, one of the protons of the methylene at the 3-position and the protons of the methylene at the 1-position of the propane skeleton) 3.8–3.87 (multiplet, 1H, the proton of the methine at the 2-position of the propane skeleton)

Test Example and Comparison Test Example

Comparison Test of Cool-Feeling Activity:

When a diluted aqueous solution (10, 20, 30, 40, or 50 ppm) of each test sample of (2S)-3-l-menthoxypropane-1,2-diol obtained in Example 1 described above (hereinafter, is referred to as "(2S) isomer" in the test example), (2R)-3-l-menthoxypropane-1,2-diol obtained in Reference Example 1 described above (hereinafter, is referred to as "(2R) isomer"), and 3-l-menthoxypropane-1,2-diol of a racemic modification (made by Takasago International Corporation, hereinafter, is referred to as "racemic modification") was prepared and the sensory intensity (the intensity of cool feeling) was compared by special panelists (10 flavorists of twenties in age) using a pair test (i.e., a method of simultaneously or successively showing 2 kinds of samples to the panelists, making select by plural panelists which had a more intensive sensitivity once per one panelist, and determining whether or not there was a difference between the 2 samples by the result; the method described in *Shinban (New Edition) Kanno-Kensa (organoleptic Test) Handbook.*, 249–252(1973), edited by Nikkagiren Kanno-Kensa Iinkai), 4 panelists answered that the cool-feeling intensity of the solution of 20 ppm of the (2R) isomer matched the cool-feeling intensity of the solution of 10 ppm of the (2S) isomer and 6 panelists answered that the cool-feeling intensity of the solution of 30 ppm of the (2R) isomer matched the cool-feeling intensity of 10 ppm of the (2S) isomer. Also, 2 panelists answered that the cool-feeling intensity of 10 ppm of the (2R) isomer matched the cool-feeling intensity of 10 ppm of the racemic modification and 8 panelists answered that the cool-feeling intensity of 20 ppm of the (2R) isomer matched that of the solution of 10 ppm of the racemic modification.

That is, it can be said that the cool-feeling intensity of the (2S) isomer is from 2 to 3 times superior to that of the (2R) isomer and is from 1.5 to 2 times superior to that of the racemic modification. Thus, it has been confirmed that the effect of the compound of the present invention has a significant difference as compared with the other compounds.

EXAMPLE 2

|  | (parts by weight) |
|---|---|
| Calcium Phosphate | 500 |
| Carboxymethyl Cellulose | 10 |
| Sodium Laurylsulfate | 20 |
| Glycerol | 250 |
| Saccharin | 2 |
| Tooth Paste Flavor X-9135 (Flavor made by Takasago International Corporation) | 8 |
| (2S)-3-l-Menthoxypropane-1,2-diol | 1 |
| Water | ad 1000 |

The components described above were mixed by a blender according to the foregoing formulation to provide a tooth paste. When the product was used as a tooth paste, an excellent refreshing effect was obtained.

EXAMPLE 3

|  | (parts by weight) |
|---|---|
| Gum Base | 230 |
| Powdered Sugar | 480 |
| Glucose | 160 |
| Starch Syrup | 118 |
| Plasticizer | 1 |
| Cola Flavor E-7002 (Flavor made by Takasago International Corporation) | 10 |
| (2S)-3-ι-Menthoxypropane-1,2-diol | 1 |
|  | 1000 |

The components described above were kneaded by a kneader according to the foregoing formulation to provide a chewing gum. When the chewing gum obtained was compared with a chewing gum without containing the compound of the present invention, in the case of the chewing gum containing the compound of the present invention, a bubble feeling like the stimulus at drinking a soda pop was added to a cola flavor and a refreshing feeling remained long in the mouth.

EXAMPLE 4

|  | (parts by weight) |
|---|---|
| A: Fine Granulated Sugar | 450 |
| Starch Syrup (water content 20%) | 370 |
| Water | q.s. |
| B: Soda Flavor E-7004 (Flavor made by Takasago International Corporation) | 1 |
| (2S)-3-ι-Menthoxypropane-1,2-diol | 0.03 |
|  | 1000 |

The components A of the foregoing formulation were compounded with each other, heat-treated to 150° C. at normal pressure by an ordinary manner, cooled, and before caking, the components B were added thereto to provide a hard candy. When the hard candy was compared with a hard candy without containing the compound of the present invention, the sharpy feeling of the Cider Flavor became mild and the bubbly feeling like the stimulus at drinking a soda pop became remarkable.

EXAMPLE 5

|  | (parts by weight) |
|---|---|
| A. Ethanol | 70 |
| Polyoxyethylene-hydrogenated Castor Oil | 5 |
| Citric Acid | 0.2 |
| Sodium Citrate | 1 |
| Methyl Parahydroxybenzoate | 1 |
| Perfume | q.s. |
| (2S)-3-ι-Menthoxypropane-1,2-diol | 2 |
| B: Glycerol | 40 |
| Propylene Glycol | 70 |
| Purified Water | q.s. |
|  | 1000 |

By uniformly dissolving each of the components A and the components B of the foregoing formulations to provide solution A and solution B, respectively. While stirring the solution B, the solution A was gradually added to the solution B, and after solubilizing the mixture, the mixed solution of filtered to provide a face lotion. When the product was used, an excellent refreshing effect was obtained.

The compound of the present invention, (2S)-3-{(1R, 2S, 5R)-[5-methyl-2-(1-methylethyl)cyclohexyl]oxy}-1,2-propanediol can be synthesized by an easy operation using easily available raw materials. Also, the compound has a property of giving an excellent cool-feeling or an excellent refreshing feeling to the skin and the mucous membrane of a human being and the compositions for oral cavity, food and drink, and cosmetics compounded with the compound of this invention have a cool-feeling or refreshing feeling, whereby the commercial values thereof are increased.

While the invention has been described in detail and with reference to specific embodiments thereof, it will be apparent to one skilled in the art that various changes and modifications can be made therein without departing from the spirit and scope thereof.

What is claimed is:

1. A process of producing (2S)-3-{(1R, 2S, 5R)-[5-methyl-2-(1-methylethyl)cyclohexyl]oxy}-1,2-propanediol represented by formula (I)

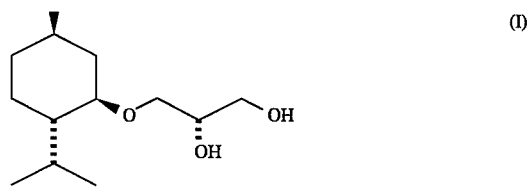

(I)

which comprises adding (1R, 2S, 5R)-5-methyl-2-(1-methylethyl)cyclohexyl alcohol to (R)-(−)-benzyl glycidyl ether represented by formula (II)

(II)

wherein Bz represents a benzyl group to provide (2S)-1-benzyloxy-2-hydroxy-3-{(1R, 2S, 5R)-[5-methyl-2-(1-methylethyl)cyclohexyl]oxy}propane represented by formula (III)

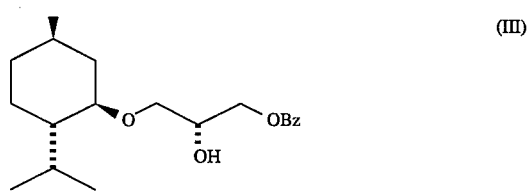

(III)

wherein Bz has the same meaning as described above, and hydrogenolyzing the product of formula (III).

* * * * *